(12) United States Patent
Palpu et al.

(10) Patent No.: US 7,658,957 B2
(45) Date of Patent: Feb. 9, 2010

(54) ANTI-ARTHRITIC HERBAL COMPOSITION AND METHOD THEREOF

(75) Inventors: Pushpangadan Palpu, Lucknow (IN); Rao Chandana Venkateswara, Lucknow (IN); Govindarajan Raghavan, Lucknow (IN); Ojha Sanjeev Kumar, Lucknow (IN); Rawat Ajay Kumar Singh, Lucknow (IN); Reddy Gaddam Dayanad, Lucknow (IN); Mehrotra Shanta, Lucknow (IN)

(73) Assignee: Council of Scientific & Industrial Research, Rafi Marg (IN)

( * ) Notice: Subject to any disclaimer, the term of this patent is extended or adjusted under 35 U.S.C. 154(b) by 0 days.

(21) Appl. No.: 12/019,409

(22) Filed: Jan. 24, 2008

(65) Prior Publication Data

US 2008/0118588 A1 May 22, 2008

Related U.S. Application Data

(62) Division of application No. 11/021,622, filed on Dec. 23, 2004, now Pat. No. 7,338,674.

(51) Int. Cl.
*A61K 36/906* (2006.01)
*A61K 36/00* (2006.01)

(52) U.S. Cl. .................................. 424/756; 424/725
(58) Field of Classification Search .................. None
See application file for complete search history.

(56) References Cited

U.S. PATENT DOCUMENTS

| 5,494,668 | A | * | 2/1996 | Patwardhan | 424/756 |
| 6,274,177 | B1 | * | 8/2001 | Wu et al. | 424/756 |
| 6,482,421 | B2 | * | 11/2002 | Weidner | 424/401 |
| 6,596,313 | B2 | * | 7/2003 | Rosenbloom | 424/464 |
| 2001/0046523 | A1 | * | 11/2001 | Newmark et al. | 424/756 |
| 2004/0014684 | A1 | * | 1/2004 | Prabhakar et al. | 514/25 |
| 2004/0156920 | A1 | * | 8/2004 | Kane | 424/725 |

OTHER PUBLICATIONS

Rege et al. Phytotherapy Res. 1999. vol. 13, pp. 275-291.*
Srivastava et al. Int. J. Crude Drug Res. 1990. vol. 28, pp. 135-137.*
Ghosh et al. Ind. J. Pharmac. 1981. vol. 15, No. 4, pp. 391-402.*
Internet publication entitled "Herbal Monograph-Vitex negundo". 2002. 1 page. Obtained from website www.himalayahealthcare.com.*

Atal, C., et al., "Screening of Indian Plants for Biological Activity: Part VIII," *Indian Journal of Experminental Biology*, 1978, vol. 16, pp. 330-349.
Chaturvedi, G.N. and R.N. Singh, "Experimental Studies on the Antiarthritic Effect of Certain Indigenous Drugs," *Ind. Jour. Med. Res.*, 1965, vol. 53(1), pp. 71-80.
Dasgupta, B., "Chemical Investigation of *Pluchea Lanceolata* I. Isolation of a New Quarternary Base, Pluchine," *Experientia*, 1967, vol. 23, pp. 989-991.
Dasgupta, B., et al., "Chemical Investigation of *Pluchea Lanceolata*, II. Identity of Pluchine with Betaine Hydrochloride," *Experientia*, 1968, vol. 24, p. 862.
Ghosh, D., et al., "Anti-Inflammatory and Analgesic Activities of Gangetin-A Pterocarpenoid from *Desmodium Gangeticum*", *Ind. J. Pharmac.* (1981), vol. 15(4), pp. 391-402.
Karandikar, G., et al., "Anti-Inflammatory Activity of Some Ayurvedic Remedies and their Influence on the Hypophyseo-Adrenocortial Axis in White Rats," *Inc. Jour. Med. Res.*, 1960, vol. 48(4), pp. 487-487.
Prasad, D.N., "Preliminary Photochemical and Pharmacological Studies on *Pluthea Lanceolata*, Linn,* " *Ind. Jour. Med. Res.*, 1965, vol. 53(11), pp. 1062-1068.
Prasad, D.N., "A Study of Anti-Inflammatory Activity of Some Indigenous Drugs in Albino Rats," *Ind. Jour. Med. Res.*, 1966, vol. 54(6), pp. 582-590.
Prasad, S. and R. Mitra, "Pharmacognostical Studies on Rasna (*Pluchea Lanceolata*. C.B. Clarke & Olive," *Jour. Res. Ind. Med.*, 1970, vol. 5(1), pp. 59-76.
Prasad, S., et al., "Pharmacognostic Study of Leaves of *Pluchea Lanceolata* C.B. Clarke & Olive (Rasna), " *Jour. Res. Ind. Med.*, 1970, vol. 4(2), pp. 203-207.
Rege, N.N., et al., "Adaptogenic Properties of Six *Rasayana* Herbs used in Ayurvedic Medicine", *Phytotherepy Research*, (1999), vol. 13, pp. 275-291.
Singh, R.H. and G.N. Chaturvedi, "Inhibition of Formaldehyde Induced Arthiritis by Certain Indigenous Drugs," *Ind. Jour. Med. Res.*, 1966, vol. 54(2), pp. 188-195.
Srivastava, V., et al., "Anti-Inflammatory Activity of *Pluchea lanceolata*: Isolation of an Active Principle", *Int. J. Crude Drug Res.*, (1990), vol. 28, pp. 135-137.
Internet website "Herbal Monograph-Vitex Negundo" (2002).

* cited by examiner

*Primary Examiner*—Christopher R. Tate
(74) *Attorney, Agent, or Firm*—Alston & Bird LLP

(57) ABSTRACT

The invention provides a novel herbal composition for treatment of arthritis and inflammation. The herbal composition comprises a therapeutically effective combination of extracts obtained from the plants *Terminalia chebula, Pluchea lanceolata, Desmodium gangeticum, Vitex negunto* and *Zingiber officinale*, optionally along with pharmaceutically acceptable additives. The invention further comprises methods of making the herbal composition and methods of use for the treatment of arthritis and inflammation.

8 Claims, No Drawings

ANTI-ARTHRITIC HERBAL COMPOSITION AND METHOD THEREOF

CROSS-REFERENCE TO RELATED APPLICATION

This application is a divisional of U.S. application Ser. No. 11/021,622, filed Dec. 23, 2004, which is hereby incorporated herein in its entirety by reference.

FIELD OF INVENTION

The present invention relates to development of an anti-arthritic herbal composition.

BACKGROUND OF THE INVENTION

Osteoarthritis (OA) is the breakdown of the joint articular cartilage. This results in the release of matrix components and their degradation products into the synovial fluid where they may become exposed to the immune system and lead in some instances to an autoimmune response by the patient (Bannerji et al, Journal of Rhuematology 33: 36.39, (1992); Poole, Osteoarthritis, W. B., Saunders, pp 155-189 (1992)). Disease activity in OA patient and their response to drug treatments have been monitored using clinical and radiologic methods of assessment (Theiler et al, Osteoarthritis cartilage, 3: 1757-1774 (1994)). More recently however biochemical assays, which quantified PG epitopes ad matrix proteins in joint synovial fluid has been employed to follow disease progression (Setnikar, International Journal of Tissue Reaction, 14:253-261 (1992)). Although these biochemical markers have afforded important data on the turnover of cartilage and bone in OA joints, they cannot provide information on the cellular events that may be responsible for the abnormal metabolism of these tissues. Further more therapeutic agents whose mechanism of action may include effects on leukocyte populations are not readily amenable to study using these biochemical markers.

A large number of nonsteroidal anti-inflammatory drugs are currently used for the treatment of OA as first-line therapy; however several adverse effects limit their clinical usefulness. NSAID's do not slow the damage to the joints or change the course of the disease (Setnikar, International Journal of Tissue Reaction, 14:253-261 (1992)). Despite the ability of these drugs to improve the symptoms of the disease, their capacity to positively influence the progression of OA has been questioned (Anderson et al., Current Therapeutic Research, 58: 93-107 (1997)). Moreover the deleterious effects of some NSAIDs on gastric mucosa and other organs have been of concern particularly during chronic usage of these drugs that is normally a prerequisite of the OA patient. Alternatively drug treatments have included intra-articular injections of hyaloroan or superoxide dismutase or daily oral administration of glucosamine sulphate al of which have been reported to provide symptomatic relief in OA patients. However the ability of these drugs to improve the underlying pathological causes of OA in patients or animal models has not been clearly demonstrated.

Hence there is an urgent need for a candidate preferably from the herbal source used in the traditional system of medicine with beneficial effects with minimum side effects. Plant based drugs have reported to exhibit minimum side effects and believed to be safe and are in use for thousands of years in the traditional system of medicine.

SUMMARY OF THE INVENTION

The present invention provides an herbal composition useful in the treatment of arthritis and inflammation. The herbal composition comprises a therapeutically effective combination of extracts obtained from the plants *Terminalia chebula, Pluchea lanceolata, Desmodium gangeticum, Vitex negunto* and *Zingiber officinale*, optionally along with pharmaceutically acceptable additives. The invention further comprises methods of making the herbal composition and methods of use for the treatment of arthritis and inflammation.

DETAILED DESCRIPTION OF THE INVENTION

The main object of the present invention is to provide a novel anti-arthritic herbal composition useful as an anti-inflammatory agent and provide relief in pain. Another object of the present invention is to provide a method of preparing an herbal composition useful as an anti-inflammatory agent and provide relief in pain. Another object of the present invention is to provide a method of treatment for arthritis using the composition of the present invention. Another object of the present invention is to provide a method of treatment for inflammation using the composition of the present invention.

*Pluchea lanceolata* was used in synergistic combination with other known plant parts or their extracts to form a pharmaceutically effective composition. Accordingly, studies were undertaken to develop a oral composition containing herbal drugs along with additives for oral ingestion to treat acute arthritis (Remington, The science and practice of pharmacy, 19$^{th}$ edition, Vol II. pp. 1635, 1995; Anonymous. Indian Pharmacopoeia. Govt of India, 1996).

*Pluchea lanceolate*—Family: Compositae

Botanical description: Erect undershrub, 30-100 cm. high, stem and branches teretc, ashy and pubescent found in sandy or saline soils in Punjab, upper Gangetic plain, Rajasthan and Gujrat. Leaves-sessile, very coriaceous, 25-27 by 0.6-1.6 cm oblong or lanceolate, obtuse apiculate narrowed at the base, finely ashy, pubescent on both sides, entire or toothed rotind the apex main nerves prominent, Inflorescence-heads in compotiicl coryinbs, involucre contracted at the mouth. Outer bracts 2-3 scriate, oblong, very obtuse, pubescent, usually tinged with ptirple, the inner most bracts linear, sub-acute, few pappus hairs distinctly connote at the base. Occurs gregariously in vast areas in dried tracks forming thickets and is considered a troublesome weed.

Phytochemistry: The petroleum ether extract of the plant on saponi-ficatioii with strong alkali, ether treatment, chromatographic analysis on aluminium hydroxide by clution with different solvents give different fractions—compound A (m.p. 92-930 C) Compound B (m.p. 217-2210) probably taraxosterol and Compound C (m.p. 147-1500 C) b-sitosterol. The same author reported the isolation of tertiary bases and a large number of water soluble quarternary bases, including pitichine, which has been identified with betaine hydrochloride Quercetin and isorhamentin are present as aglycones in the leaves. Glycosides and tannins were absent.

Pharmacology: Early studies on the water soluble fraction of the ethanol extract of the whole plant showed two main effects—a spasmolytic action on the smooth muscle, and an acetylcholine like action. On exposure to this fraction relaxation occurred in the isolated ileum of rabbit and rat, isolated rat uterus, and in situ ileum in the dog. Phenobarbital induced hypnosis was enhanced. Significant experimental data are reported on the role of this plant extracts on induced arthritis. The decoction of the whole plant in a dose of 1.5 mg (0.75 g. of the dry powder) given to non-adrenalectomised dogs for 10 days was most effective against formalin arthritis. The response was evaluated by a lessening of swelling of ankle joints and limb volume. In albino rats, the water soluble fraction of the 90% alcohol extract showed significant anti-inflammatory activity in induced formalin arthritis and granuloma pouch. Comparison with betamethasone, showed a lower mortality rate of 1 out of 12, as against 12 out of 29 given betamethasone. Gastric side effects-ulcer and bleeding occurred in 5 out of 12 rats given the *Pluchea lanceolata* extract and in 10 out of 12 rats exposed to betamethasone. An important clinical difference was that the plant extract suppressed the delayed periarticular changes more as compared to the acute inflammatory phase. Another study on the therapeutic aspect of *Pluchea lanceolata* was the comparison of the water-soluble fraction of the alcoholic extract with the non-saponifiable steroidal fraction, the test system being carageenan-produced hind paw oedema in albino rats. While the former extract did not show significant activity the latter steroidal fraction was significantly anti-inflammatory in action. It had, however, not much effect on the granuloma pouch. The anti-inflammatory potential of some ayurvedic compositions containing *P. lanceolata* extract was tested on experimental arthritis and granuloma pouch. These showed marked anti-inflammatory activity in both models. The decoction of the plant has been used in arthritis. The leaves are aperients and used as a laxative, analgesic and antipyretic.

*Desmodium gangeticum*—Family: Leguminosae

Botanical description: A common shrub, 2-4 ft. high found almost throughout India ascending to 5000 ft. in the Himalayas. It is very variable and is met in its various forms in forests and wastelands.

Phytochemistry: 5-methoxy-N,N-dimethyltryptamine, N,N-dimethyltryptamine, their N-oxides, N-methyl-tetrahydroharman, 6-methoxy-β-carbolinium cation (regenerated from Reinecke salt) from aerial parts. Alkaloids isolated from aerial parts were found responsible for anticholinesterase, smooth muscle stimulant, CNS stimulant and depressor responses in test animals. Tert-β-phenylethylamines and candicine present in roots, responsible for nicotine like effects on dog intestine in situ and carotid blood pressure. A new pterocarpan-gangetin-isolated and characterized as 7α,12α-dihydro-13-methoxy-3,3-dimethyl-11-(3-methyl-2-butenyl)-3H, 7H-benzofuro[3,2-C]pyrano[3,2-g]benzopyran-10-ol. Twelve alkaloids of our structural types (carboxylated and decarboxylated tryptamine, β-carbolines and β-phenylethylamines) isolated. Two pterocarpanoids—gangetinin and desmodin—isolated and their structures determined. A new antifungal isoflavanoid phytoalexin desmocarpin was isolated together with genistein, 2'-hydroxygenistein, dalbergioiden, diphysolone and kievitone from fungus-inoculated leaflets; its structure determined. 24-ethylcholesta-5,22-dien-3β-ol, 24-ethylcholest-5-en-3β-ol and 24-methylcholest-5-en-3β-ol was isolated. A novel flavone glycoside, 4',5,7-trihydroxy-8-prenyl-flavone 4'-O-α-L-rhamnopyranosyl-(1→6)-β-D-glucopyranoside was isolated from the stem of *Desmodium gangeticum*.

Pharmacology: An inhibitory influence of gangetin over the reproductive organs is believed to be attributed primarily to the antiprolactin nature of gangetin and secondarily to the significant fall in plasma testosterone level caused by gangetin. Daily administration of gangetin (0.5, 1, 1.5 and 2 mg/kg body weight for 30 days) caused and impairment of fertility and also caused a reduction in the vaginal sperm count and an enhancement of Pre-implantation losses. Complete recovery of fertility was evident 30 days after the withdrawal of gangetin treatment.

*Vitex negundo*—Family: Verbenaceae

Botanical description: A small tree or a large shrub with an irregular trunk, stem and branches covered with thin grey bark, the branches quadrangular and finely hoary down. Leaves—petiolate, shorter opposite, exstipulate, diginately three to five foliate. Flowers—Bracteate, bracts 1.4 to 2.5 mm long, lanceolate and cauducou bisexual, bluish, purple. Fruit—aglobose, ovoid or obovoid, four chambered, four seeded drupe. It is found throughout the greater part of India ascending to an altitude of 1500 m in the outer Himalayas.

Medicinal uses: Patients with rheumatoid arthritis were treated with the plant and encouraging results obtained. Nirgundi decoction has been used for steam bath for arthritis or joints pains. In 40 cases of gridhrasi (sciatica) the plant was found quite effective. The plant's role in curing katisula has been particularly mentioned in Vaidya Manorama. Dried leaves when smoked are also said, to relieve catarrh and headache. Oil prepared with the juice is applied to sinuses and scrofulous sores. Oil is used also as bathing oil for rubbing on the head and in cervical lymphadenitis. Oil is found to him useful for sloughing wounds and ulcers.

Phytochemistry: Alkaloids, reducing sugars, glycosides, flavonoids, sterols, resins and tannins are present. 6-8-dimethyl ether of delphinidin and J, —A dimethyl ether of leucoeyanidin 1-0 rhumano-glucosides have been isolated besides three new flavone glycosides.

Pharmacology: The essential oil from the leaves was found to have antifungal activity against *Trichoderma* spp, *Fusafium helmin*-thosporium, limited activity on bacteria. 3,5,7 trihydroxy-4,6,8-trimethoxy flavone isolated from the seeds showed estrogenic activity. However, in comparison to 17-0 estradiol it is an extremely weak estrogen. At oral dose of 200 mg/kg for two days, the seed extract inhibited ovulation in 60% of the treated animals. Recently it was reported that the ethylacetate extract showed a significant activity against carrageenin, 5-HT and bradykinin-induced inflammatory oedema. It also possessed significant inhibitory effect against granuloma pouch and cotton pellet implantation though less potent than both phenylbutazone and beta-methasone.

*Zingiber officinale*—Family: Zingiberaceae

Botanical description: It is a small plant. The leaves are green, slender, flat and elongated. The stem is smooth and solid. The bulbs are composed of several bulbils (cloves), encased in white or pink skin of the parent bulb. The inflorescence is an umbel initially enclosed in a spathe. Ginger has been under cultivation from times immemorial.

Medicinal uses: The therapeutic value of ginger in functional gastrointestinal disorders was studied in 29 patients. A significant carminative effect, with a relief of nausea, gascolic, flatulence, belching and heaviness was observed. The effects of fried and raw ginger on blood showed an increase in fibrinolytic activity in 20 patients with ischaemic heart disease. A decrease in triglycerides and cholesterol has been observed. Ginger oil drops are put in the ears for infection and earache. Ginger is also used as an anti-infective agent topically and in other intercurrent infections.

Phytochemistry: The strong smelling juice of the bulbs contains a mixture of aliphatic mono and polysulphides. The chief constituent is allicin, diallyl disulphide oxide. The latter results from spontaneous enzymatic reduction of allin and 5-allylcystine sulphamide. Thio-glycoside, aminoacids, fatty acids, flavonols, vitamins, trace elements, volatile oils etc. have also been demonstrated.

Pharmacology: Antibacterial and antifungal activity of ginger has been shown, by several investigators, against many common pathogenic organisms such as *Staphylococcus aureus, Escherichia coli, Candida albicans, Shigelia sonnei*, and *Salmonella typhi*. Essential oils of ginger prevented an increase in a -lipoproteins, pre- a lipoproteins occurring after cholesterol-feeding in rabbits. Fibrinolytic activity was also significantly increased. Inhibition of platelet-aggregation in vitro and in vivo has also been demonstrated with ginger. There have been several studies showing the hypoglycaemic activity of ginger and allicin in animals.

*Terminalia chebula*—Family: Combretaceae

Botanical description: It is a moderate or large deciduous tree, attaining 25-30 m in height. Leaf buds, branches and youngest leaves are covered with soft, shining rust coloured hairs. Leaves 7-20 cm, glabrous, opposite, elliptic-oblong, rounded, acute apex. Flowers bisexual, white or yellow with an offensive smell. Fruit is a drupe, pendulous, 2-4 cm long, obovoid from a broad base, glabrous, sribbed, when dry, yellowish green, bark 6 mm thick, dark brown, many generally shallow vertical cracks. *T. chebula* is found in the sub-Himalayan tracks from the Ravi eastwards to West Bengal and Assam, ascending up to an altitude of 1500 m in the Himalayas. In the deciduous forests of India, it attains a girth of 1.5-1.8 m with a bole of 9 m.

Medicinal uses: The plant is used extensively in the preparation of many Ayurvedic compositions for infectious diseases such as chronic ulcers, leucorrhoea, pyorrhoea and fungal infections of the skin'. Short term clinical trials have been carried out on patients with simple constipation. Haritaki increases the frequency of stools and has got the property of evacuating the bowel completely. The total response of the drug is excellent in 90% cases and good in 80% cases. No side effects were noted. Triphala is an important composition in the Ayurvedic pharmacopoeia containing haritaki. Triphala and each of its constituents are well known rasayana drugs. They are used to prevent aging and impart longevity, immunity and body resistance against disease. They have beneficial effects on all the tissues.

Phytochemistry: Fruits contain about 30% of astringent substances—chebulinic acid, tannic acid, gallic acid etc. Resin and a purgative principle of the nature of anthraquinone and sennoside are also present.

Pharmacology: Various extracts have been prepared from the powdered fruits. It contains a constituent, which has a wide anti-bacterial and antifungal spectrum, and also inhibits growth of *E. coli*, the most common organism responsible for urinary tract infection. The oil in the kernel increased the motility, of the gastrointestinal tract of the mouse. The action was comparable with castor oil. The oil by itself is non-irritant but releases an irritant principle when incubated with lipase. The laxative activity of Triphala has been tested on albino mice. The laxative activity is also exhibited by the fruit pulp.

Accordingly, the main embodiment of the present invention relates to a synergistic herbal composition useful for the treatment of arthritis, said composition comprising a therapeutically effective amount of extracts obtained from the plants *Terminalia chebula, Pluchea lanceolata, Desmodium gangeticum, Vitex negundo* and *Zingiber officinale*, optionally along with pharmaceutically acceptable additives.

In one embodiment the extracts are selected from powdered plant parts or lyophilized extracts of plants *Terminalia chebula, Pluchea lanceolata, Desmodium gangeticum, Vitex negundo* and *Zingiber officinale*. In one embodiment, the plant extracts are obtained from plant parts selected from leaf, rhizome and aerial parts.

In another embodiment, the additives are selected from binders, diluents and lubricants. In further embodiments, the binders used include starch, starch paste, gum acacia and carboxy methyl cellulose, the diluent used include lactose, and the lubricants used include starch and lactose.

In another embodiment, the composition treats inflammation, arthritis, and acts as a free radical scavenger.

In yet another embodiment, the extracts of the plants are mixed in the ratio *Pluchea lanceolata* 2-4 wt. %, *Desmodium gangeticum* 2-5 wt. %, *Vitex negundo* 2-4 wt. %, *Zingiber officinale* 2-5 wt. %, and *Terminalia chebula* 4-9 wt %, along with conventional additives to form an oral dosage form.

In yet another embodiment, the composition is in an oral or topical dosage form including tablets, capsules, powders, liquids, ointments, or creams.

In another embodiment, the plant extracts are 50% aqueous alcoholic extract. In a further embodiment the alcohol used is ethanol.

Still another embodiment involves where the plant extracts comprise about 10-27% wt of the total composition.

In another embodiment, a method is provided for preparing an herbal composition wherein the said method comprises the steps of:
a. drying the plant material in shade;
b. powdering the dried plant material to a coarse powder;
c. extracting the powdered dried plant material;
d. concentrating the obtained extract; and
e. lyophilizing the concentrated extract to obtain herbal composition.

In a further embodiment, step (c) of this method involves extraction with 40-50% aqueous alcohol at 25-30° C. In a further embodiment, step (c) of this method involved extraction with aqueous alcohol in the ratio of 1:8 to 1:15 for 4-7 days. In a further embodiment, step (d) of this method is carried out under reduced pressure at 40-60° C.

In a further embodiment, a method for the treatment of arthritis or inflammation is provided comprising the step of administering any herbal composition of the present invention as described elsewhere herein to a subject in need thereof. In a further embodiment, the subject in need thereof is a human or an animal. In yet another embodiment, the composition is administered orally or topically. In yet another embodiment, the composition is administered at a daily dosage level ranging from 25 mg/kg body weight to 100 mg/kg body weight.

In a further embodiment, the herbal compositions of the present invention show activity as potent antioxidants and potent mucoprotectants. In another embodiment, the herbal compositions of the present invention show efficacy in the protection of adjuvant induced chronic arthritis as well as in the treatment of chemical mediator-induced arthritis. In still another embodiment, the herbal compositions of the present invention show potent anti-inflammatory activity in acute and chronic inflammation. In still another embodiment the herbal compositions of the present invention show efficacy in the treatment of simple pain acting centrally and peripherally.

Compositions

The first step in the preparation of the following compositions involves a process for making the plant material suitable for formulating into a tablet or capsule. The specified portion of the plant was collected and dried under shade at room temperature (about 25° C.-about 35° C.) for 72 hours or until the material was dry. The material was then powdered into a fine powder. A specified amount of the powdered material was then extracted exhaustively with about 50% aqueous alcohol at room temperature (at about 25° C.-about 35° C.). Extraction was carried out in a closed container immersing specified amount of the plant material in specified solvent (at about 1:8-about 1:15 ratio) for about 4-about 7 days. At the end of this stage, solvent was decanted and filtered if necessary to make it free from plant debris. The solvent was then concentrated by evaporating under vacuum at less than about 40-about 60° C. The concentrate was then freeze dried to obtain final product in powder form. The final product was then made into oral dosage form by using it as an ingredient for making tablets and capsules. Suitable binders like starch and diluents like lactose were added to make up the composition.

Composition (F1):

| | |
|---|---|
| *Pluchea lanceolata* | 3 wt. % |
| *Desmodium gangeticum* | 4 wt. % |
| *Vitex negundo* | 3 wt. % |
| *Zingiber officinale* | 4 wt. % |
| Starch paste | 15 wt. % |
| Talc | 1 wt. % |
| Lactose | q.s. to make 100% |

*Pluchea lanceolata, Desmodium gangeticum, Vitex negundo,* and *Zingiber officinale* were collected and dried in shade. The dried material (1 Kg) was then powdered and extracted with about 50% aqueous alcohol (3 L) for 5 days. At the end of this, the solvent was decanted and filtered if necessary to remove the plant debris. The extract was then concentrated under vacuum at less than about 50° C. Then the extract was lyophilised to obtain the extract in powder form. About 15 g of starch was mixed with water and heated to form a paste. The weighed quantities of the plant extracts were then blended with starch paste and then lactose was added in a quantity sufficient to make about 100 g. The ingredients were then mixed properly with the starch paste to form a mass. The mass was then granulated in a granulator and then dried at about 104° F. and screened through a 16 mesh screen. Talc was added to the dried granules and then they were punched in a tablet punching machine to form uniform tablets.

Composition (F2):

| | |
|---|---|
| *Pluchea lanceolata* | 3 wt. % |
| *Desmodium gangeticum* | 4 wt. % |
| *Vitex negundo* | 3 wt. % |
| *Zingiber officinale* | 4 wt. % |
| *Terminalia chebula* | 7 wt. % |
| Starch paste | 15 wt. % |
| Talc | 1 wt. % |
| Lactose | q.s. to make 100% |

*Pluchea lanceolata, Desmodium gangeticum, Vitex negunto, Zingiber officinale* and *Terminalia chebula* were collected and dried in shade. The dried material (1 Kg) was then powdered and extracted with 50% aqueous alcohol (3 L) for 5 days. At the end of this, the solvent was decanted and filtered if necessary to remove the plant debris. The extract was then concentrated under vacuum at less than 50° C. Then the extract was lyophilised to obtain the extract in powder form. The weighed quantities of the plant extracts as mentioned were mixed with the diluent lactose and then were filled in hard gelatin capsules and dispensed.

The invention is further extrapolated in the form of examples. The following examples are offered by way of illustration and not by way of limitation. As such, the forgoing examples should not be construed to limit the scope of the present invention.

EXAMPLES

Example 1

Anti-Inflammatory Activity

Methods

Anti-inflammatory activity was studied using a carrageenin induced rat paw edema method. One group received phenyl butazone in the dose of 100 mg/kg body weight as a standard. Another group received only the vehicle and served as an untreated control. Yet another group received the test composition. After one hour 0.1 ml of 1% suspension of carrageenin in 0.5% carboxy methyl cellulose was injected in the planter aponeurosis of right hind paw. The paw volume was measured before and after four hours of carrageenin treatment by plethysmograph. Results are shown in Tables 1 and 2.

Results

Table 1 shows the effects of compositions F1 and F2 on carrageenin induced paw edema.

TABLE 1

| Treated Group | Dose (mg/kg) | % Edema (Swelling) |
|---|---|---|
| Control | — | 62.4 ± 2.9 |
| F1 | 25 | 56.3 ± 3.7 |
| | 50 | 50.2 ± 3.1 |
| F2 | 25 | 35.4 ± 2.2$^a$ |
| | 50 | 21.0 ± 1.1$^b$ |
| Ibuprofen | 30 | 25.3 ± 2.3$^b$ |

Values are mean ± S.E.M. for six rats.
P: $^a$<0.01 and $^b$<0.001 compared to the respective control group.
Note that no mortality was found in any of the treated groups, and no gross abnormality in behavior was observed in the animals exposed with herbal compositions.

As described elsewhere herein, the composition F1 contains the extracts of *Pluchea lanceolata, Desmodium gangeticum, Vitex negundo* and *Zingiber officinale*, while the composition F2 additionally contains extracts of *Terminalia chebula*. The results of Table 1 show that the composition F2 produced a significant reduction in the percentage of paw edema at the 25 and 50 mg/kg doses. Therefore, composition F2 is highly effective and showed a significant result compared to F1. For comparison, results with Ibuprofen are also shown. Although these results were similar to composition F2 in reducing edema, the disadvantage of using Ibuprofen is that it causes ulcer in the stomach while composition F2 does not.

Table 2 shows the effect of individual plant extracts and composition (F1) on carrageenin-induced paw edema.

TABLE 2

| Treated Group | Dose (mg/kg) | % Reduced Swelling |
|---|---|---|
| Control | — | 62.4 ± 2.9 |
| *P. lanceolata* | 200 | 53.5 ± 4.1 |
| *D. gangeticum* | 200 | 51.2 ± 3.9 |
| *V. negunto* | 200 | 54.8 ± 4.2 |
| *Z. officinale* | 200 | 56.6 ± 4.0 |
| *T. chebula* | 200 | 55.1 ± 4.1 |

Values are mean ± S.E.M. for six rats.
The individual components *Pluchea lanceolata, Desmodium gangeticum, Vitex negundo* and *Zingiber officinale* did not show any significant activity.

Example 2

Procedures for Measuring Anti-Arthritic Activity

Formaldehyde-induced arthritis was produced in rats by injecting 0.1 ml of 2% formaldehyde in the hind paw under the planter aponeurosis. Paw volume was measured daily for 13 days. The test composition was given 24 hours before formalin injection and continued for 13 days. Results are shown in Tables 3 and 4.

Results

Table 3 shows the effect of compositions F1 and F2 on paw edema in formaldehyde-induced acute arthritis.

TABLE 3

| Treated Group | Dose (mg/kg) | % Edema (Swelling) |
| --- | --- | --- |
| Control (no treatment) | — | 110.8 ± 7.9 |
| F1 | 25 | 99.20 ± 5.9 |
|  | 50 | 80.00 ± 4.6 |
| F2 | 25 | 43.40 ± 2.8$^a$ |
|  | 50 | 20.20 ± 1.8$^b$ |
| Ibuprofen | 30 | 27.80 ± 4.2$^b$ |

Values are mean ± S.E.M. for six rats.
P: $^a$<0.01 and $^b$<0.01 compared to the respective control group.
Note that no mortality was found in any of the treated groups, and no gross abnormality in behavior was observed in the animals exposed with herbal compositions.

As described elsewhere herein, the composition F1 contains the extracts of *Pluchea lanceolata, Desmodium gangeticum, Vitex negundo* and *Zingiber officinale*, while the composition F2 additionally contains extracts of *Terminalia chebula*. The results of Table 3 show that composition F1 did not produce a significant reduction percent edema at the doses of 25 and 50 mg/kg. However, the composition containing the active component *Terminalia chebula* produced a significant result compared to the control. For comparison, results with Ibuprofen are also shown. Although the result for 30 mg/kg of Ibuprofen was similar to the 50 mg/kg dose of composition F2, the disadvantage of using Ibuprofen is that it causes ulcer in the stomach while composition F2 does not.

Table 4 shows the effect of individual plant extracts and compositions on paw edema in formaldehyde-induced acute arthritis.

TABLE 4

| Treated Group | Dose (mg/kg) | % Reduced Swelling |
| --- | --- | --- |
| Control | — | 110.8 ± 5.6 |
| P. lanceolata | 200 | 98.5 ± 5.7$^a$ |
| D. gangeticum | 200 | 95.2 ± 4.7$^a$ |
| V. negunto | 200 | 101.8 ± 5.2 |
| Z. officinale | 200 | 103.5 ± 5.8 |
| T. chebula | 200 | 101.1 ± 6.1 |

Values are mean ± S.E.M. for six rats.
P: $^a$<0.01 compared to the respective control group.

Synergy

Composition F2 which contains *Pluchea lanceolata, Desmodium gangeticum, Vitex negunto, Zingiber officinale* and *Terminalia chebula* showed a very potent result of decrease in swelling and the result is similar to Ibuprofen. Therefore the combination is highly effective in treatment of arthritis and inflammation. However, Ibuprofen is a modern synthetic drug whose side effects include ulceration (it is an ulcer causing agent). Although composition F1 produced some reduction in swelling, composition F2 produced a statistically significant reduction demonstrating the synergistic and unexpected results of the combination of F2 versus F1.

The invention claimed is:

1. A composition comprising a combination of plant extracts, wherein said combination comprises
    (a) 2-4 weight % of at least one plant extract derived from the plant *Pluchea lanceolata;*
    (b) 2-5 weight % of at least one plant extract derived from the plant *Desmodium gangeticum;*
    (c) 2-4 weight % of at least one plant extract derived from the plant *Vitex negundo;*
    (d) 2-5 weight % of at least one plant extract derived from the plant *Zingiber officinale;* and
    (e) 4-9 weight % of at least one plant extract derived from the plant *Terminalia chebula.*

2. The composition of claim 1, wherein said combination contains a therapeutically effect amount of plant extracts for treating arthritis or inflammation.

3. The composition of claim 1, wherein said composition acts as a free radical scavenger.

4. The composition of claim 1, wherein said plant extracts are obtained from leaf, rhizome or aerial plant parts.

5. The composition of claim 1, further comprising a pharmaceutically acceptable additive, wherein said additive is a binder, a diluent, or a lubricant.

6. The composition of claim 1, wherein said composition is formulated for oral delivery, and wherein said composition is in the form of a tablet, a capsule, a powder, or a liquid.

7. The composition of claim 1, wherein said composition is formulated for topical delivery, and wherein said composition is in the form of an ointment or a cream.

8. The composition of claim 1, wherein said composition comprises a plant extracts in an amount from about 10 weight % to about 27 weight %, and wherein said plant extracts comprises at least one plant extract derived from each of the following plants: *Terminalia chebula, Pluchea lanceolata, Desmodium gangeticum, Vitex negundo* and *Zingiber officinale.*

* * * * *